(12) United States Patent
Choi

(10) Patent No.: US 6,572,585 B2
(45) Date of Patent: Jun. 3, 2003

(54) REMOTE-CONTROLLED PORTABLE AUTOMATIC SYRINGE DEVICE

(76) Inventor: Soo Bong Choi, #5-908, Youwon Apt. 421-7 Yeonsoo-dong, Chungju-shi, Chungcheongbuk-do (KR)

( * ) Notice: Subject to any disclaimer, the term of this patent is extended or adjusted under 35 U.S.C. 154(b) by 0 days.

(21) Appl. No.: 09/942,473

(22) Filed: Aug. 29, 2001

(65) Prior Publication Data

US 2003/0014013 A1 Jan. 16, 2003

(30) Foreign Application Priority Data

Jul. 12, 2001 (KR) .......................... 2001-42135

(51) Int. Cl.[7] .............................................. A61M 37/00
(52) U.S. Cl. ...................................... 604/131; 604/151
(58) Field of Search .............................. 604/30, 65–67, 604/134, 131, 151–156; 417/15, 33, 42, 43, 44.11, 63; 700/281–285; 137/625.64, 625.65

(56) References Cited

U.S. PATENT DOCUMENTS 4,417,889 A 11/1983 Choi
4,602,700 A * 7/1986 Szabo .......................... 185/38
5,662,612 A * 9/1997 Niehoff ....................... 604/151

FOREIGN PATENT DOCUMENTS

JP 52-3292 1/1977

* cited by examiner

Primary Examiner—Brian L. Casler
Assistant Examiner—Michael M Thompson
(74) Attorney, Agent, or Firm—Sheridan Ross PC

(57) ABSTRACT

Disclosed is an automatic syringe device including a syringe pump having a housing defined therein with a syringe receiving chamber for receiving a syringe, a control unit received in the housing and adapted to control a motor adapted to supply, to the syringe pump, a drive force for injecting a liquid medicine out of the syringe, a transmitter/receiver unit received in the housing and electrically connected to the control unit, and a remote controller adapted to control the control unit via the transmitter/receiver unit. The remote controller includes a transmitter/receiver unit adapted to conduct transmission and reception of signals to and from the control unit of the syringe pump via the transmitter/receiver unit of the syringe pump, a control unit adapted to control the transmitter/receiver unit of the remote controller, and a display adapted to display an ON or OFF state.

6 Claims, 19 Drawing Sheets

REMOTE-CONTROLLED PORTABLE AUTOMATIC SYRINGE DEVICE

BACKGROUND OF THE INVENTION

1. Field of the Invention

The present invention relates to a portable automatic syringe device, and more particularly to a remote-controlled portable automatic syringe device including a syringe pump configured to dispense with any display means while operating in a remote controlled fashion and a remote controller adapted to control the syringe pump and provided with a display, thereby being capable of allowing the user to conveniently control the syringe pump by use of the remote controller while viewing the display without a requirement to expose the syringe pump for a manipulation thereof, so that the privacy of the user can be secured.

2. Description of the Prior Art

Automatic syringe devices, which enable an injection of liquid medicine for a prolonged time, are well known. Typically, known automatic syringe devices have a configuration in which a push means for pushing a syringe piston is coupled to a housing receiving an injection syringe. For example, such automatic syringe devices are disclosed in Japanese Utility Model Laid-open Publication No. Sho. 52-3292 and U.S. Pat. No. 4,417,889. The syringe device disclosed in Japanese Utility Model Laid-open Publication No. Sho. 52-3292 has inconvenience in carrying it because it has an injector mounted outside a basic case, thereby requiring a double case structure. In order to solve such a disadvantage, an automatic syringe device requiring no double case structure has been proposed, as in the above mentioned U.S. Pat. No. 4,417,889. FIGS. 1 and 2 illustrate a control circuit and a structure of the automatic syringe device disclosed in U.S. Pat. No. 4,417,889, respectively. Referring to FIG. 1, the output of an oscillator A1 is coupled to a timer A2 which is, in turn, coupled at its output to a digital comparator A3. The digital comparator A3 also receives an output from a fixed number switch A4. The output of the digital comparator A3 is connected to a counter A6 and an R/S flip-flop A9. Another oscillator A5 is also provided which has an output coupled to counters A6 and A13, and AND gates A10 and A11. The flip-flop A9 is reset by an output from a digital comparator A7. Another R/S flip-flop A16 is also provided which is reset by an output from a digital comparator A14 coupled to the counter A13. A control unit A17 is also coupled to the counter A13. The control unit A17 serves to activate the counter A13 in accordance with an operation of a manual infusion switch A12. The control unit A17 applies its output to the counters A13 and A16. The output from the control unit A17 is also sent to a counter A21. The output of the counter A21 is coupled to a digital comparator A22 which is, in turn, coupled to a step motor driver A19 for driving a step motor A20. The output of the flip-flop A16 is coupled to one input of the AND gate A11, which is also coupled at the other input thereof to the oscillator A5. The output of the AND gate A11 is coupled to one input of an OR gate A18. Fixed number switches A15 and A25 are connected to the digital comparators A14 and A22, respectively. Each of the fixed number switches A4, A8, A15, and A25 has five protruding insert bars and serves to provide a reference value for an associated one of the digital comparators A3, A7, A14, and A22. A light source A24 and a photo sensor A23 are coupled to the counter A21 in order to provide sensing results thereof to the counter A21, respectively. Referring to FIGS. 2 and 3, the arrangements of the light source A24 and photo sensor A23 are illustrated. As shown in FIGS. 2 and 3, the light source A24 and photo sensor A23 are arranged in such a fashion that they face each other while being vertically spaced from each other. A gear plate, which is included in a gear mechanism G, is interposed between the light source A24 and photo sensor A23. The gear plate has a plurality of through holes A26 uniformly spaced from one another in a circumferential direction, as shown in FIG. 3. The gear plate is fixedly fitted around a gear shaft A27 having a screw portion. A piston plate A28 is threadedly coupled to the gear shaft A27 in the form of a nut in such a fashion that it slides along the screw portion of the gear shaft A27 when the gear shaft A27 rotates. The rotation of the gear shaft A is carried out by a drive force from the motor A20 transmitted via the gear mechanism G. The driving of a motor M (corresponding to the motor A20 in FIG. 1) is controlled by the operations of the counter A21, digital comparator A22, switch A25, and motor drive A19. The above mentioned elements of the syringe device are received in a housing, as shown in FIG. 2. In particular, the light source A24 and photo sensor A23 are fixedly mounted at an upper portion of the housing by means of a bracket fixed to the housing. In this syringe device, a liquid medicine, such as insulin, contained in a syringe I is outwardly injected through an injection needle N connected to the syringe I, by a sliding movement of the piston plate A28. In such a syringe device, however, the housing and syringe I thereof are exposed to ambient air. As a result, moisture and water are likely to penetrate into the syringe device. For this reason, there is inconvenience in that if the user desires to take a shower while the syringe is in place, then the housing should be contained in a separate sealing case.

In order to solve such a problem, a sealable syringe device has been proposed by the applicant. Such a sealable syringe device is illustrated in FIG. 4 which is a front view. Referring to FIG. 4, the syringe device includes a cover 10 sealably coupled to the upper end of a housing 20, and a bottom cover 40 sealably coupled to the lower end of the housing 20. A connector 2, to which a feeding tube 1 is integrally connected, is threadedly coupled to the cover 10. The connector 2 communicates with a syringe 21 received in the housing 20. A piston 22 is slidably fitted in the syringe 21. A liquid medicine to be injected is contained in the syringe 21. A power transmission means 30 is mounted on the bottom surface of the housing 20. The power transmission means 30 has a rotating shaft 31 to which a disc type push means 50 is threadedly coupled. The disc type push means 50 moves vertically by a rotation of the rotating shaft 31, thereby vertically moving the piston 22.

Referring to FIG. 5, which is a plan view of FIG. 4, the cover 10, to which the connector 2 connected with the feeding tube 1 is connected, is arranged on the left portion of the upper surface of the housing 20. A battery cover 24 is arranged on the right portion of the upper surface of the housing 20.

FIG. 6 is a cross-sectional view taken along the line A—A of FIG. 5. As shown in FIG. 6, the cover 10 is centrally provided with a threaded hole 11 in which the connector 2 is threadedly fitted at its lower end. The threaded hole 11 has threads 11-1. The connector is formed, at its lower end, with threads 2-15 to be threadedly coupled with the threads 11-1 of the threaded hole 11. The cover 10 is also provided at its lower end with a bolt portion 12 threadedly fitted in the upper end of the housing 20. A packing 13 is fitted around the bolt portion 12 of the cover 10 between the lower end of the cover 10 and the upper end of the housing 20. A syringe receiving chamber 23 is defined in the interior of the housing 20. The push means 50 is fitted in the lower end of the housing 20 in such a fashion that it slides vertically in the housing 20. The housing 20 is also formed at its inner surface with a vertical push means guide groove 25 adapted to guide a vertical movement of the push means 50 and vertical piston guide grooves 27 adapted to guide a vertical movement of the piston 22.

FIG. 7 shows a detailed configuration of the power transmission means 30a mounted on the bottom surface of the housing 20 and a detailed configuration of the push means 50 threadedly coupled to the rotating shaft 31 of the power transmission means 30. As shown in FIG. 7, the push means 50 includes a lower disc 54 threadedly coupled to the rotating shaft 31 in such a fashion that it slides vertically along the rotating shaft 31. The lower disc 54 is provided at its periphery with a guide protrusion 51 engaged in the guide groove 25 of the housing 20 and adapted to guide the vertical movement of the lower disc 54. The push means 50 also includes an upper disc 55 integrally formed with the lower disc 54. The upper disc 55 is provided at its periphery with an engagement means 52. The upper disc 55 is fitted in a sleeve plate 26 (FIG. 8) fixed to the lower end of the piston 22 in such a manner that its engagement means 52 engages with a mating engagement means formed on the inner peripheral surface of the sleeve plate 26. The sleeve plate 26 is also provided at its outer peripheral surface with protrusions engaging with the guide grooves 27 respectively. The power transmission means 30 includes a reduction mechanism 33 for transmitting the rotating force of a motor (not shown) to the rotating shaft 31 in a speed-reduced manner.

In order to use the syringe device having the above mentioned configuration, the piston 22, which is in a state separated from the housing 20, is first fitted in the syringe 21, which is also in a state separated from the housing 20, in such a manner that it is completely inserted into the syringe 21. In this state, a disposable injection needle (not shown) is fitted onto the tip 21-1 of the syringe 21. Thereafter, the injection needle is penetrated into the interior of a phial through the plug of the phial. In this state, the piston 22 is pulled to suck a liquid medicine (for example, insulin) contained in the phial into the syringe 21.

The piston 22, which is in a state fitted in the syringe 21 containing the liquid medicine, is then inserted into the syringe receiving chamber 23 of the housing 20 in such a manner that it is seated on the push means 50. Subsequently, the cover 10 is threadedly coupled to the upper end of the syringe receiving chamber 23. The connector 2 is then threadedly fastened to the cover 10. As the connector 2 is threadedly fastened to the cover 10, it is fitted onto the syringe tip 21-1. Thus, the syringe 21 is maintained in a sealed state in the housing 20. When the motor (not shown) is operated under the above condition, the push means 50 moves upwardly, thereby upwardly pushing the piston 22. As a result, the liquid medicine contained in the syringe 21 is outwardly injected from the syringe 21. At this time, the upward movement of the push means 50 is accurately carried out because its guide protrusion 51 engages with the guide groove 25. Since respective protrusions of the sleeve plate 26 slide along the piston guide grooves 27 shown in FIG. 6, the upward movement of the piston 22 is also accurately carried out.

Meanwhile, FIG. 9 illustrates an example of a conventional injection needle unit used for portable automatic syringe devices enabling a prolonged injection of a liquid medicine. As shown in FIG. 9, the injection needle unit includes a feeding tube 1, a "-" shaped straight injection needle member (called a "straight butterfly-shaped injection needle") 3 connected to one end of the feeding tube 1, and a connector 2 connected to a connector portion 20-5 of the housing 20.

In order to use such an injection needle unit, the user himself angularly penetrates the straight butterfly-shaped injection needle member 3 into the subcutaneous tissue while observing the penetration of the injection needle member 3 with the naked eye. The reason why the user observes the penetration of the injection needle member 3 with the naked eye is because the injection needle member 3 has a straight shape. However, such an observation is very uncomfortable. The straight butterfly-shaped injection needle member 3 is also likely to move in the subcutaneous tissue of the user because it penetrates the subcutaneous tissue of the user at an angle. In this case, the subcutaneous tissue may be damaged. In severe cases, blood may flow out of the subcutaneous tissue. The user may also feel a severe pain.

As mentioned above, the conventional injection needle unit has a drawback in that it is difficult to smoothly inject insulin because the injection needle member 3, which penetrates the subcutaneous tissue of the user at an angle, may be easily blocked at its tip by the subcutaneous tissue. To this end, the feeding tube of such a conventional injection needle unit inevitably has an increased diameter. However, such a feeding tube having an increased diameter results in a possibility of an excessive insulin injection. In addition, this may result in wastage of expensive insulin. For instance, where it is desired to inject insulin into the user using an automatic syringe device equipped with the above mentioned injection needle unit, it is necessary to completely vent air existing in the feeding tube 1 and injection needle member 3 before penetrating the injection needle member 3 into the subcutaneous tissue of the user. To this end, insulin, which is contained in the syringe device, is outwardly discharged through the feeding tube 1 and injection needle member 3, thereby venting air. In this case, a large amount of insulin is wasted where the conventional injection needle unit having the diameter-increased feeding tube is used.

In order to solve this problem, an injection needle unit has been proposed which has an L-shaped injection needle. Such an injection needle unit is illustrated in FIGS. 10 and 11, respectively. As shown in FIGS. 10 and 11, the injection needle unit includes a feeding tube 1, an injection needle member 3 connected to one end of the feeding tube 1, and a connector 2 connected to the other end of the feeding tube 1.

In the case of the injection needle unit shown in FIGS. 10 and 11, the injection needle member 3 has an injection needle 3-11 having an L-shaped structure shown in FIG. 12. This injection needle 3-11 has a first portion, namely, a horizontal portion, fitted in a connecting rib 3-12 integrally formed with one end of the feeding tube 1, and a second portion, namely, a vertical portion, provided with a needle tip. The injection needle 3-11 is provided with a curved portion 3-13 at its horizontal portion fitted in the connecting rib 3-12, as shown in FIG. 11. A depressing member 3-14 is integrally formed with the connecting rib 3-12 in such a fashion that the injection needle 3-11 protrudes perpendicularly from the depressing member 3-14. The depressing member 3-14 is depressed against the skin of the user upon penetrating the injection needle member 3 into the subcutaneous tissue. A bacterial infection prevention member 3-14-1, which is made of a sterile nonwoven fabric, is attached to the surface of the depressing member 3-14 which comes into contact with the skin of the user upon penetrating the injection needle unit 3 into the subcutaneous tissue. The connector 2, which is connected to the other end of the feeding tube 1, has a male thread 2-15. The connector 2 is protected by a protection cap 2-17 which has a female thread 2-16 threadedly coupled to the male thread 2-15 of the connector 2. In use, the connector 2 is threadedly coupled to a connector portion 20-5 of a housing 20 included in an automatic insulin syringe device. The connector portion 20-5 of the housing 20 has a female thread 20-5a threadedly coupled to the male thread 2-15 of the connector 2. In FIG. 10, the reference numeral "3-18" denotes a needle protection cap.

Where it is desired to inject insulin contained in the automatic insulin syringe device using the above mentioned injection needle unit, the protection cap 2-17 is first separated from the connector 2, which is, in turn, threadedly coupled to the connector portion 20-5 of the housing 20. Thereafter, the needle protection cap 3-18 is separated from the injection needle 3-11. The user then penetrates the injection needle 3-11 into the subcutaneous tissue while depressing the depressing member 3-14 against the skin by hand. At this time, the injection needle 3-11 penetrates vertically into the subcutaneous tissue of the user because it has an "L" shape. Accordingly, the user can carry out the penetration of the injection needle 3-11 instantaneously without any observation with the naked eye. Therefore, the user feels little pain upon penetrating the injection-needle 3-11 into the subcutaneous tissue. By virtue of such a configuration of the injection needle unit 3, the automatic insulin syringe device can be conveniently used, as shown in FIG. 13. Since the injection needle 3-11 penetrates vertically into the subcutaneous tissue of the user by virtue of its "L" shape, there is no phenomenon that the injection needle 3-11 is blocked at its tip by the subcutaneous tissue of the user. Thus, the injection of insulin is smoothly carried out. Accordingly, the feeding tube can have a reduced diameter and an increased length. Since the feeding tube 1 has a reduced diameter, it is possible to minimize the wastage of insulin occurring upon venting air existing in the feeding tube 1 and injection needle 3-11 and to reduce the manufacturing costs. Since the feeding tube 1 also has an increased length, it is possible to extend the range of the applied positions of the injection needle 3-11 on the body of the user. Accordingly, it is possible to achieve convenience in use. Since the bacterial infection prevention member 3-14-1, which is made of a sterile nonwoven fabric, is attached to the depressing member 3-14, it is possible to prevent the depressing member 3-14 from coming into direct contact with the skin of the user upon penetrating the injection needle unit 3 into the subcutaneous tissue. Accordingly, it is possible to prevent the user from being infected. Since the injection needle 3-11 penetrates vertically into the subcutaneous tissue of the user by virtue of its "L" shape, as mentioned above, it hardly moves in the subcutaneous tissue, even when an external force is applied thereto. Accordingly, there is no damage of the subcutaneous tissue. Of course, there is no phenomenon that the blood flows out of the subcutaneous tissue. The user also does not feel any pain.

Referring to FIG. 14, a control circuit for automatic syringe devices is illustrated. As shown in FIG. 14, the control circuit includes a key input unit 61, a control unit 17 having a microcomputer function to recognize a key input generated from the key input unit 61, a display 63 for outputting data corresponding to the recognized key input, and displaying the data, and a ROM 65 for storing diverse data and programs. The control circuit also includes a motor drive unit 67 for driving a motor 68 under the control of a control unit 70 while controlling the rotating speed of the motor 68, and a photocoupler 69 for sensing the rotating speed of the motor 68. Preferably, the control unit 70 includes a pair of controllers, that is, a first controller 71 and a second controller 72, which have the same function, in order to maintain a desired function even when one of the controllers 71 and 72 is out of order. The controllers 71 and 72 have terminals P1 to P5 and terminals P1' and P2', respectively. These terminals are ports connected to data and/or bus lines, respectively. An example of the key input unit 61 is illustrated in FIG. 15 whereas an example of the display 63 is illustrated in FIGS. 16a and 16b. The motor 68 may be a stepping motor or a servo motor.

An algorithm adapted to conduct a control through the control circuit may be stored in the ROM 65. An example of the algorithm is illustrated in FIG. 17.

Under the condition in which the control circuit of FIG. 14 is activated as a power switch (not shown) is switched on, first and second steps S101 and S102 are sequentially executed in accordance with a manipulation of the key input unit 61 carried out by the user. When the control circuit is activated, a mode window is first displayed on the display 63 which is a liquid crystal display (LCD) in the illustrated case. A cursor is positioned on one of mode blocks displayed on the mode window. The cursor may be displayed in the form of a shaded block image, a block image of a color different from those of the mode blocks, or a block image having a size different from those of the mode blocks. The user then repeatedly manipulates a "NEXT" key 61-1 on the key input unit 61 to position the cursor on a desired one of the mode blocks. In this state, the user manipulates a "SELECT" key 61-2 to select a desired mode corresponding to the mode block on which the cursor is positioned. That is, it is determined in first step S101 whether or not a mode selection is made. Where a mode selection is made, a mode selected in accordance with the mode selection is executed in second step S102. Where the selected mode corresponds to a checking mode, that is, when the "SELECT" key 61-2 is depressed in a state in which the cursor is positioned on a "CHECKING" block in the mode window, the procedure proceeds to step S102-11. In step S102-11, it is first determined whether or not there is a confirm command for displaying the injection amount of insulin per hour set in a setting mode, thereby allowing the user to confirm the set injection amount, that is, whether or not the "SELECT" key 61-2 is depressed in a state in which the cursor is positioned on a "CONFIRM" block in a checking window. The checking window is displayed when the "CHECKING" block in the mode window is selected. When it is determined that the confirm command is generated, the injection amount per hour set in the setting mode is displayed in the form of a graph so that the user can recognize the set injection amount. Subsequently, the procedure returns to first step S101. The return to first step S101 may be executed using diverse methods. For example, the return to first step S101 may be achieved in accordance with a re-depression of the "SELECT" key 61-2. On the other hand, where no confirm command is generated, the procedure proceeds to step S102-12. In step S102-12, it is determined whether or not a replace command is generated. Where a replace command is generated, that is, when the "SELECT" key 61-2 is depressed in a state in which the cursor is positioned on a "REPLACE" block in the checking window, an initial ventilation of air existing in the syringe device is executed. Following the air ventilation, the procedure returns to first step S101. When no replace command is generated, the procedure also returns to first step S101.

Where the selected mode corresponds to an injection mode, that is, when the "SELECT" key 61-2 is depressed in a state in which the cursor is shifted from the state of FIG. 16a to an idle "INJECTION" block in the mode window in accordance with a repeated depression of the "NEXT" key 61-1, the procedure proceeds to step S102-2. In step S102-2, a general insulin injection function is executed. After completion of the insulin injection, an alarm (its alarm means is not shown) is generated to inform the user of the completion of the insulin injection. Thereafter, the procedure returns to step S101.

Where the selected mode corresponds to an exercise mode, that is, when the "SELECT" key 61-2 is depressed in a state in which the cursor is shifted from the state of FIG. 16a to an "EXERCISE" block in the mode window in accordance with a repeated depression of the "NEXT" key 61-1, the procedure proceeds to step S102-3. In step S102-3, a function to inject an amount of insulin reduced from the injection amount of insulin set in the setting mode for a set time (for example, one hour for an exercise) is executed. After the set time elapses, the procedure returns to step S101. The reduced injection amount of insulin in the exercise mode can be appropriately adjusted by manipulating an "UP" key 61-3 and a "DOWN" key 61-4 shown in FIG. 15, taking into consideration the physical constitution of the user. The reduction of the injection amount may be indicated in the form of a percentage of the set injection amount.

Where the selected mode corresponds to the setting mode, that is, when the "SELECT" key 61-2 is depressed in a state in which the cursor is shifted from the state of FIG. 16a to a "SETTING" block in the mode window in accordance with a repeated depression of the "NEXT" key 61-1, the procedure proceeds to step S102-4. In step S102-4, a setting window is displayed. If the cursor is positioned on a "BASIC" block of the setting window, the user then depresses the "SELECT" key 61-2 to set the basic injection amount at mealtime. The setting of the basic injection amount may be carried out by manipulating the "UP" key 61-3 and "DOWN" key 61-4 shown in FIG. 15 in a state in which a basic injection amount setting window is displayed, as shown in FIG. 18b. In FIG. 18b, "20u" represents the set basic injection amount under the condition in which the minimum basic injection amount corresponds to "1u". Basic data of such a display output pattern is stored in the ROM 65. When the control unit 70 designates a desired data address, data stored in the ROM 65 at the designated data address is outputted to the display 63. Such a method may be achieved using a well-known technique. After completion of the setting of the basic injection amount, the "SELECT" key 61-2 is depressed again in a state in which the cursor is shifted from the state of FIG. 18a to a "MEAL" block in the setting window in accordance with a depression of the "NEXT" key 61-1, as shown in FIG. 19a. When the "MEAL" block is selected, a mealtime injection amount setting window is displayed, as shown in FIG. 19b. In this state, a desired insulin injection amount at each mealtime is set, taking into consideration the physical constitution of the user. In FIG. 19b, the set insulin injection amount at lunch is displayed.

The automatic syringe device having the above mentioned function has an advantage in that a desired insulin injection amount is manually adjustable in accordance with the physical constitution of the user. However, the manual adjustment of the insulin injection amount may instead cause a problem in that where it is conducted by an impatient or unskilled user, the insulin injection amount may possibly be set to an excessive amount resulting in side effects harmful to the health of the user, for example, a hypoglycemic effect.

SUMMARY OF THE INVENTION

Therefore, the present invention has been made in view of the above mentioned problem, and an object of the invention is to provide an automatic syringe device including a syringe pump configured to operate in a remote controlled fashion, thereby being capable of allowing the user to conveniently control the syringe pump by use of a remote controller without a requirement to directly manipulate the syringe pump.

Another object of the invention is to provide an automatic syringe device including a syringe pump configured to dispense with any display means while receiving power supply means including a motor in a hollow extension extending longitudinally from a housing of the syringe pump, so that the syringe pump has a reduced size while being shaped into a rod structure, like as a fountain pen, to be conveniently worn by the user.

In accordance with the present invention, these objects are accomplished by providing an automatic syringe device comprising a syringe containing a liquid medicine, a syringe pump having a housing defined therein with a syringe receiving chamber for receiving the syringe, a rotating shaft received in the housing and adapted to apply, to the syringe, a drive force for injecting the liquid medicine out of the syringe in accordance with a rotation thereof, a reduction mechanism received in the housing and coupled to the rotating shaft, a motor received in the housing and adapted to supply drive power to the reduction mechanism, and a first control unit received in the housing and adapted to control an operation of the motor, further comprising:

a first transmitter/receiver unit received in the housing and electrically connected to the first control unit; and a remote controller adapted to control the first control unit via the first transmitter/receiver unit, the remote controller comprising a key input unit adapted to generate a key signal in response to a manipulation thereof conducted by a user, a second control unit adapted to receive the key signal from the key input unit and to conduct a control operation in response to the received key signal, a second transmitter/receiver unit electrically connected to the second control unit and adapted to conduct transmission and reception of signals to and from the first transmitter/receiver unit under a control of the second control unit, and a display electrically connected to the second control unit and adapted to display an ON or OFF state and an operation mode of the syringe pump under a control of the second control unit, whereby the user is allowed to control the syringe pump by use of the remote controller while viewing the display of the remote controller without a requirement to expose the syringe pump for a manipulation thereof.

Preferably, the key input unit of the remote controller comprises a "NEXT" key, a "SELECT" key, an "UP" key, a "DOWN" key, and a key input confirm key adapted to prevent an erroneous operation of the syringe pump due to an erroneous manipulation of the key input unit by the user.

Preferably, the key input unit of the remote controller further comprises position recognizing protrusions provided at opposite sides of the key input confirm key, respectively.

Preferably, the key input confirm key generates a confirm signal for allowing the control unit of the remote controller to receive a key input generated from the key input unit, when it is repeatedly depressed a predetermined number of times. The automatic syringe device may further comprise a motor housing formed at one side of the housing while extending vertically in parallel to the rotating shaft, the motor housing serving to receive the motor therein.

Alternatively, the automatic syringe device may further comprise a motor housing extending downwardly from a lower end of the housing and receiving the motor therein, and a hollow extension extending downwardly from the lower end of the housing in parallel to the motor housing and receiving the first control unit therein, whereby the syringe pump has a rod-shaped structure.

Since the remote-controlled portable automatic syringe device of the present invention includes the syringe pump configured to dispense with any display means while operating in a remote controlled fashion and the remote controller adapted to control the syringe pump and provided with the display it can allow the user to conveniently control the syringe pump by use of the remote controller while viewing the display without a requirement to expose the syringe pump for a manipulation thereof, so that the privacy of the user can be secured. Also, since power supply means including the motor is received in a hollow extension extending longitudinally from the housing of the syringe pump, the syringe pump can have a reduced size while being shaped into a rod structure, like as a fountain pen, to be conveniently worn by the user.

BRIEF DESCRIPTION OF THE DRAWINGS

Other objects and aspects of the invention will become apparent from the following description of embodiments with reference to the accompanying drawings in which:

FIG. 16b is a schematic view illustrating a checking window displayed on the display screen in response to selection of a "CHECKING" block in the mode window of FIG. 16a;

FIG. 18b is a schematic view illustrating a basic injection amount window displayed on the display screen in accordance with selection of a "BASIC" block in the basic injection amount setting window of FIG. 18a;

FIG. 19b is a schematic view illustrating a mealtime injection amount window displayed on the display screen in accordance with selection of a "MEALTIME" block in the basic injection amount setting window of FIG. 19a;

DESCRIPTION OF THE PREFERRED EMBODIMENTS

Now, the present invention will be described in detail with reference to the annexed drawings.

Figure 20:
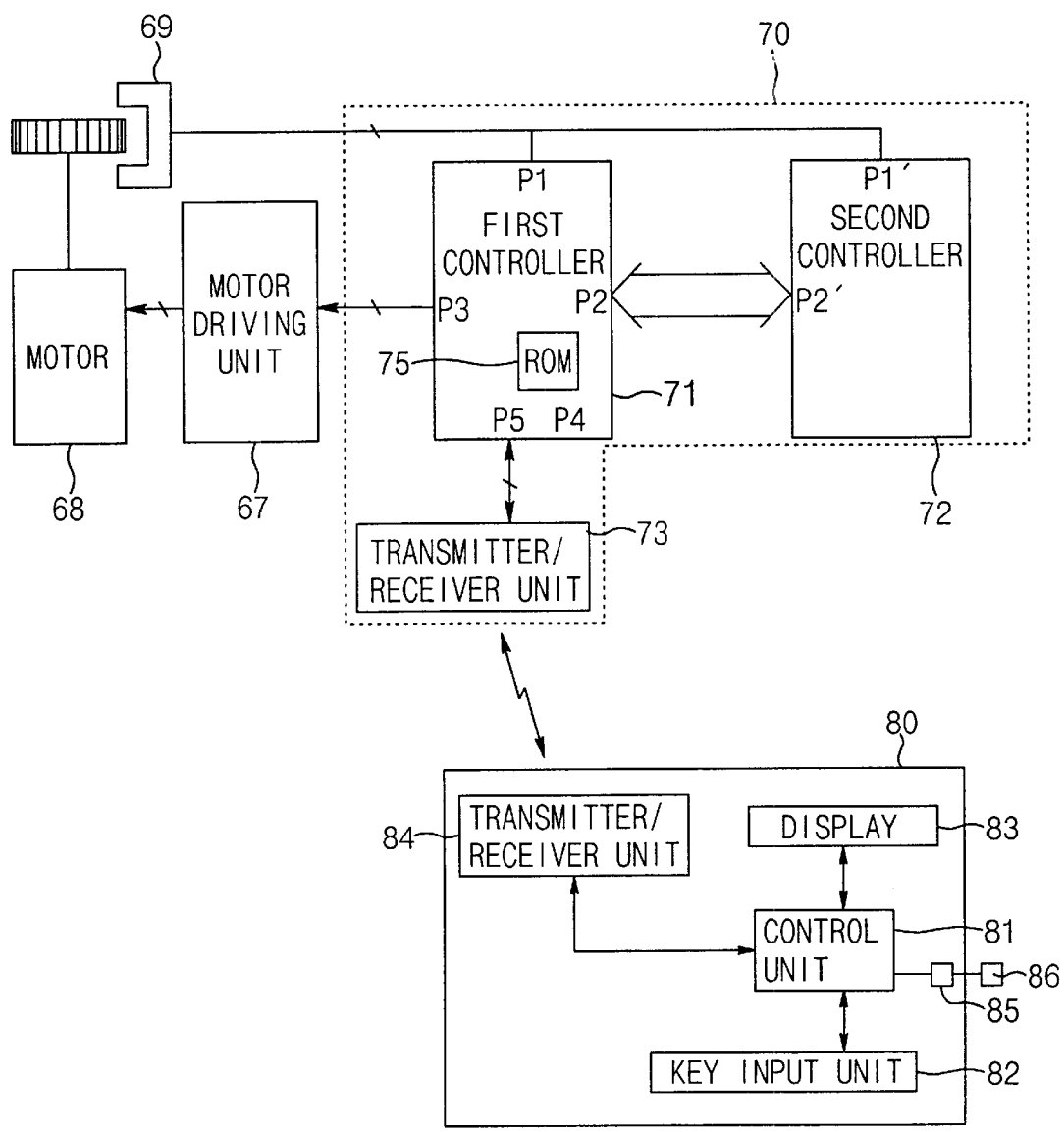
FIG. 20 is a block diagram illustrating a control circuit included in a remote-controlled portable automatic syringe device according to the present invention.
Figure 21:
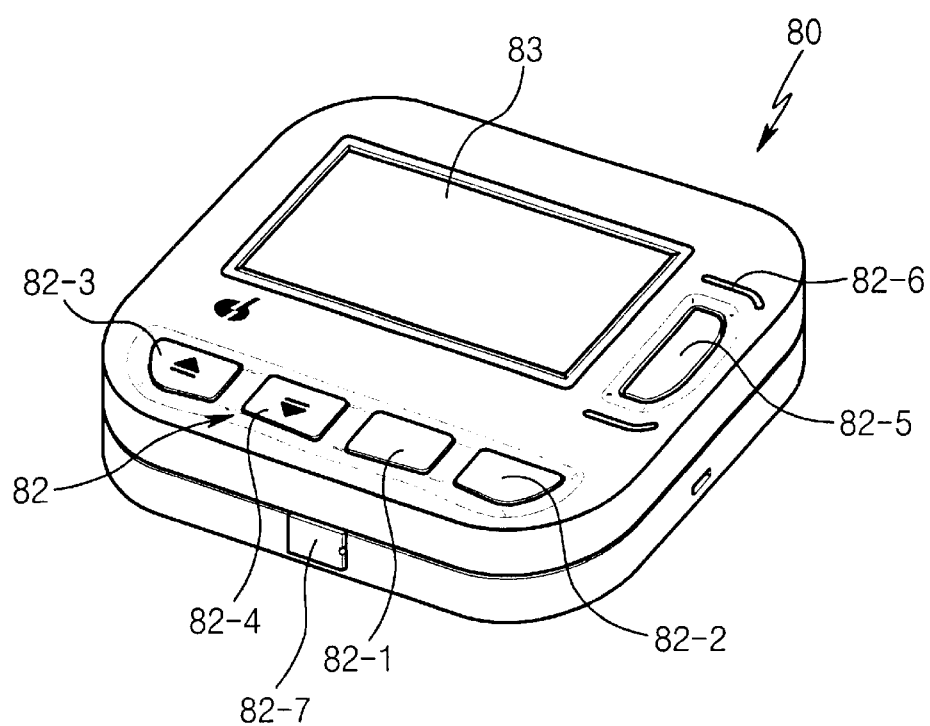
FIG. 21 is a perspective view illustrating a remote controller according to the present invention.
Figure 22:
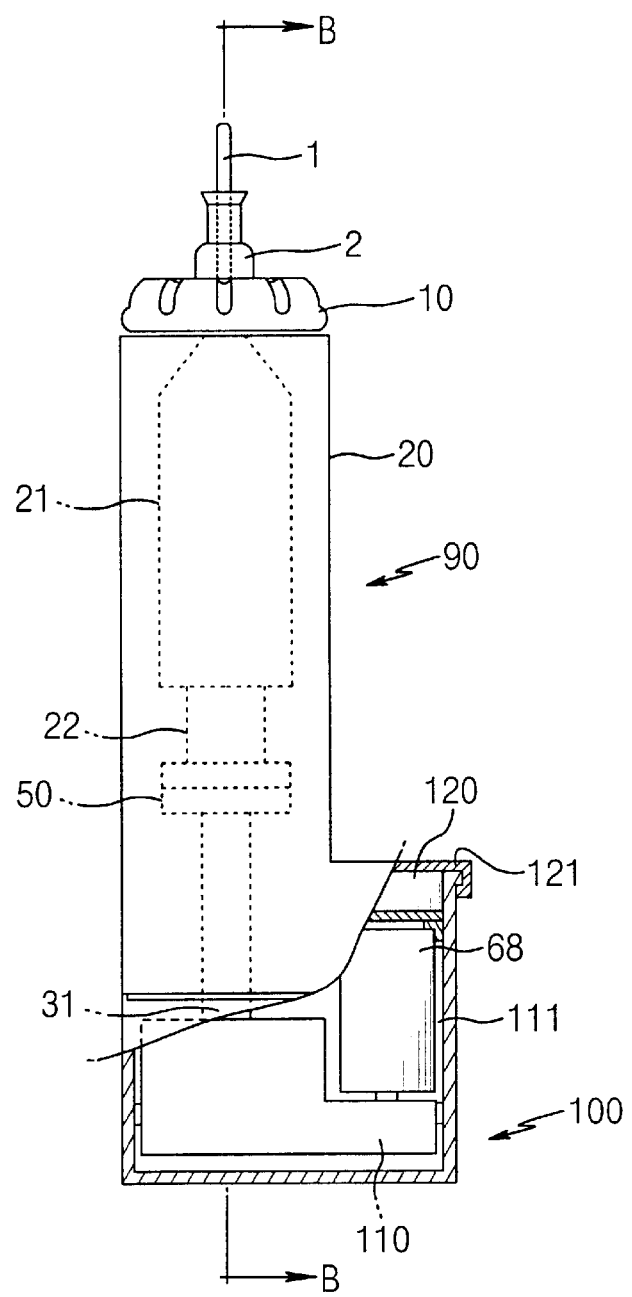
FIG. 22 is a partially-broken front view illustrating a syringe pump included in the remote-controlled portable automatic syringe device according to an embodiment of the present invention.
Figure 23:
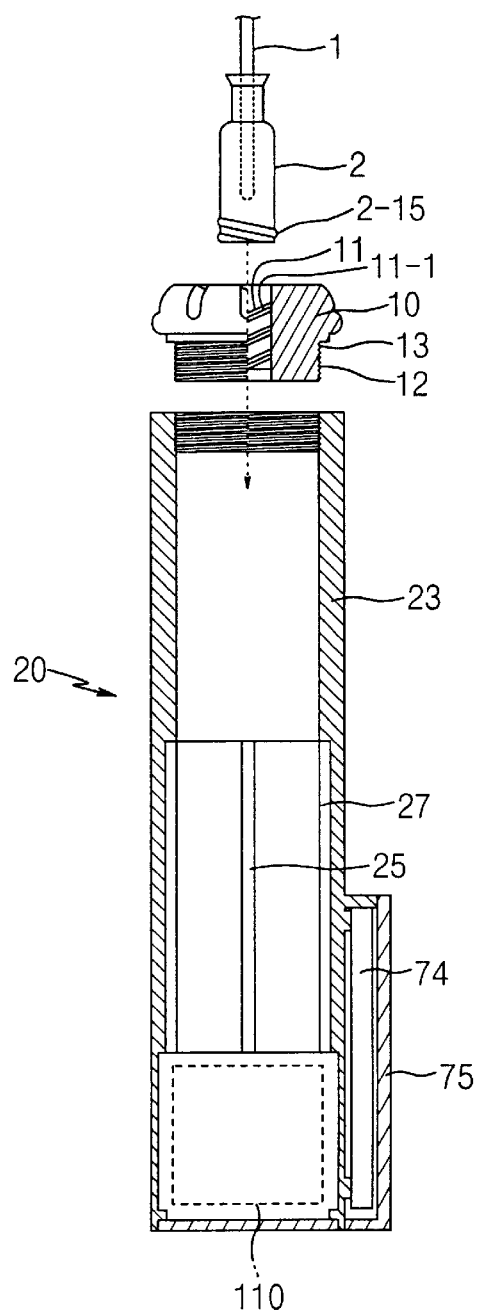
FIG. 23 is a cross-sectional view taken along the line B—B of FIG. 22.

FIG. 20 is a block diagram illustrating the circuit configuration of a remote-controlled portable automatic syringe device according to the present invention. FIG. 21 is a perspective view illustrating a remote controller according to the present invention. FIG. 22 is a partially-broken front view illustrating the automatic syringe device according to the present invention. FIG. 23 is a cross-sectional view taken along the line B—B of FIG. 22.

Figure 1:
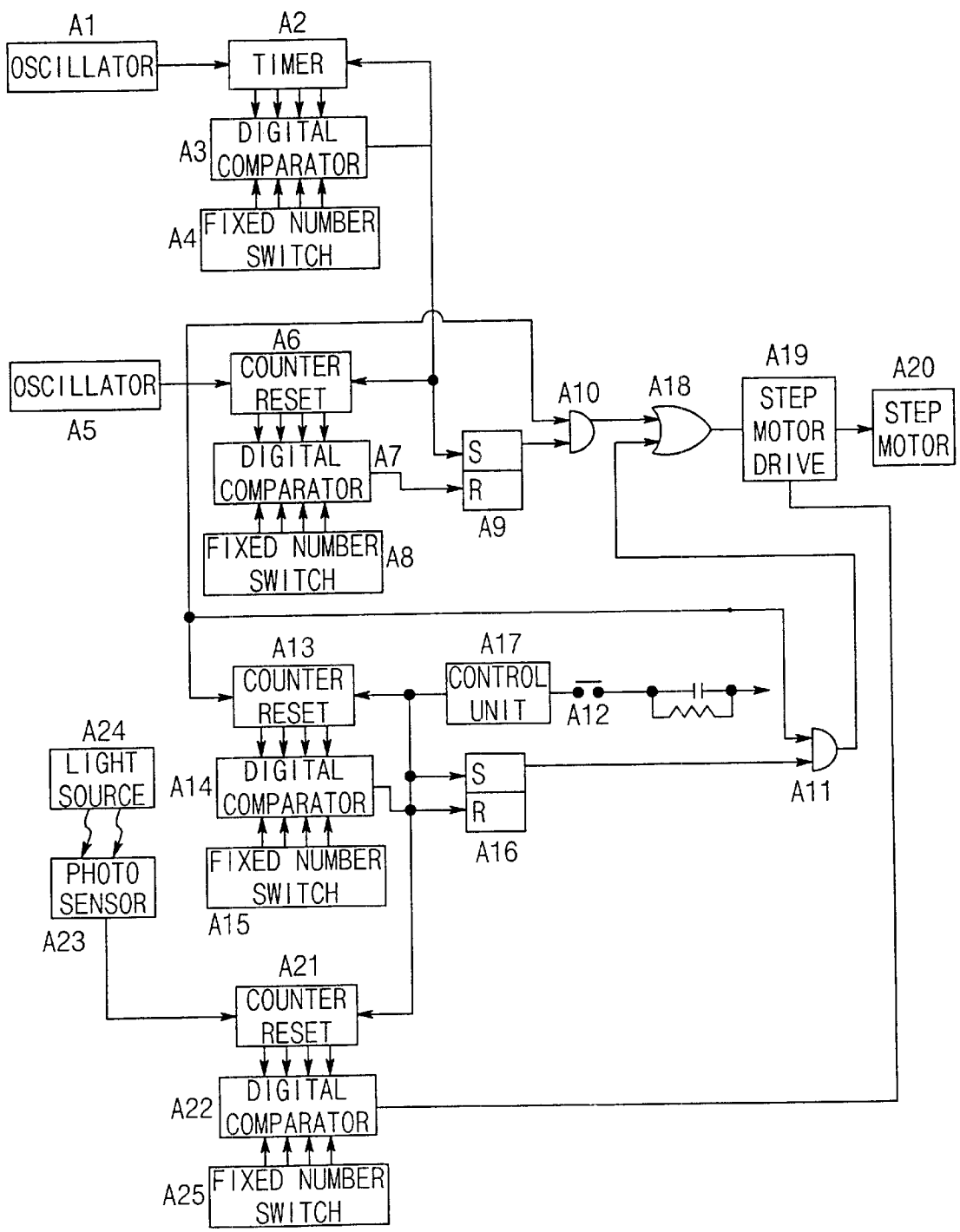
FIG. 1 is a block diagram illustrating a control circuit used in a conventional automatic syringe device.
Figure 2:
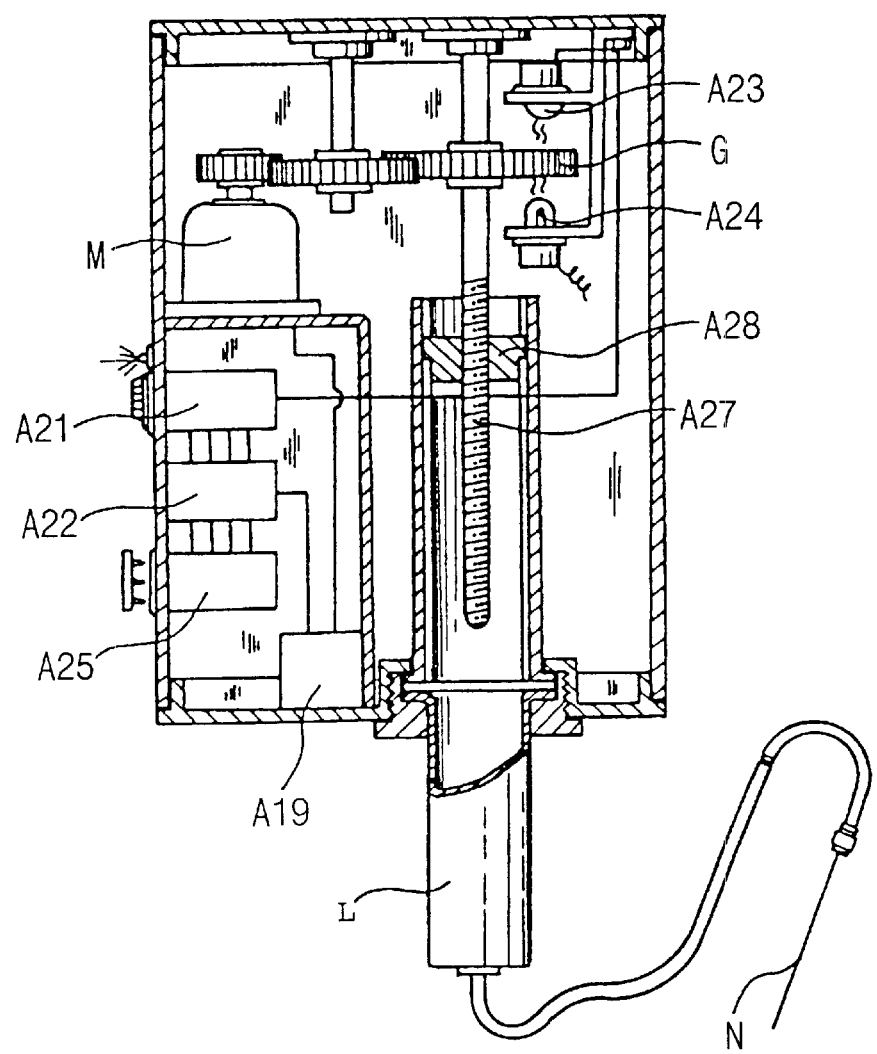
FIG. 2 is a cross-sectional view illustrating a structure of the automatic syringe device shown in FIG. 1.
Figure 3:
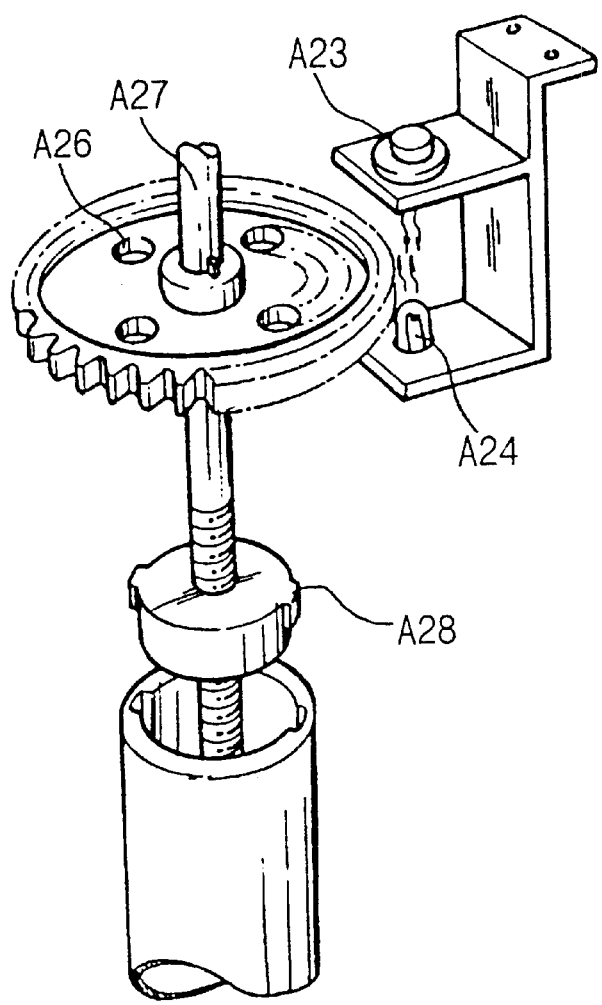
FIG. 3 is a perspective view illustrating the installation of a photo sensor in the automatic syringe device shown in FIG. 1.
Figure 4:
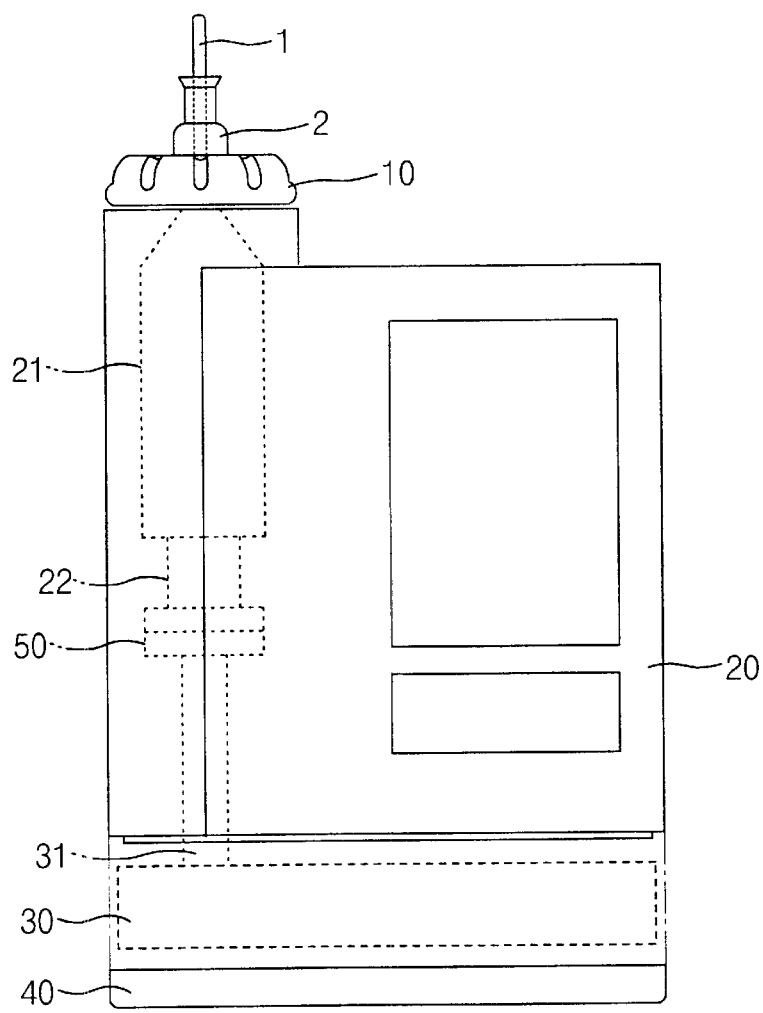
FIG. 4 is a front view illustrating another conventional automatic syringe device.
Figure 5:
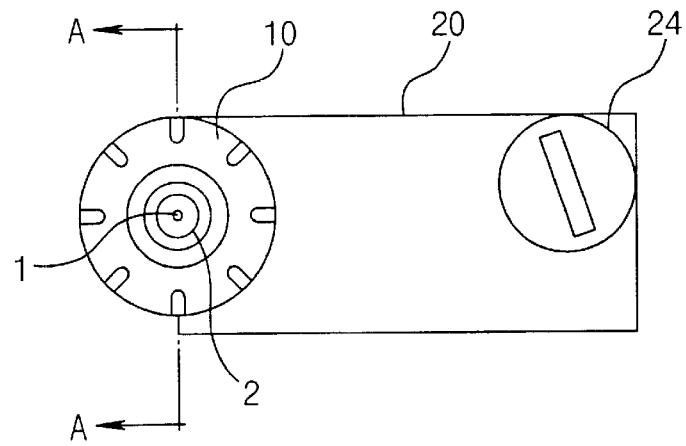
FIG. 5 is a plan view of FIG. 4.
Figure 6:
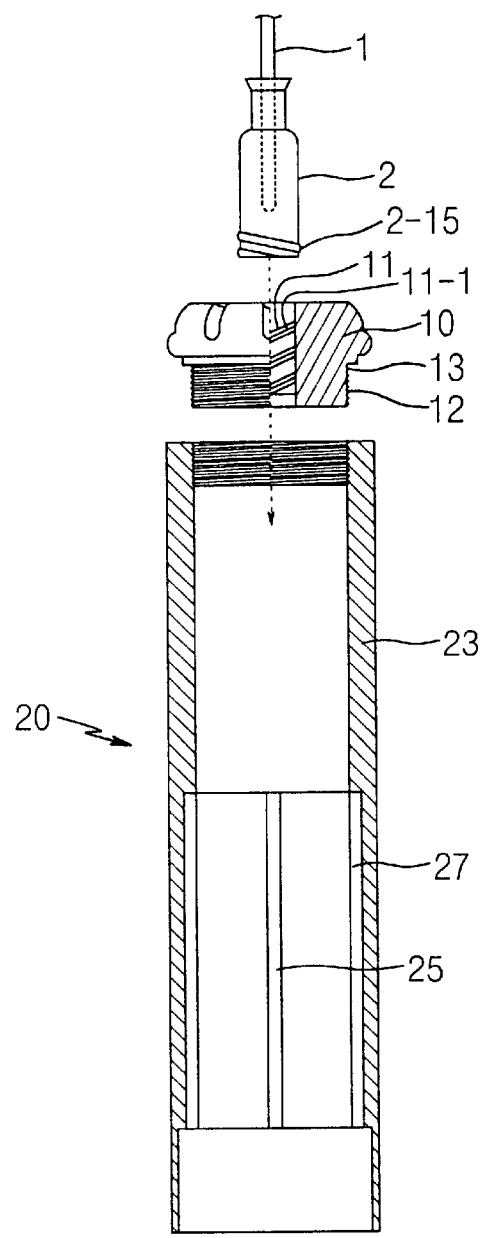
FIG. 6 is an exploded cross-sectional view taken along the line A—A of FIG. 2.
Figure 7:
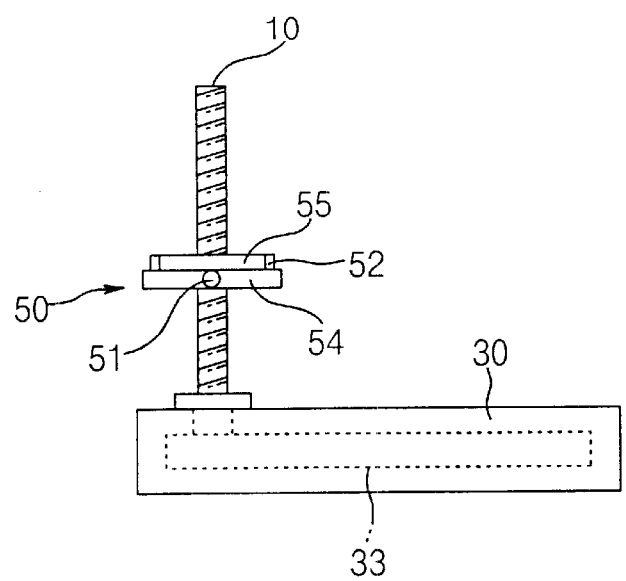
FIG. 7 is a front view illustrating a conventional power transmission means.
Figure 8:
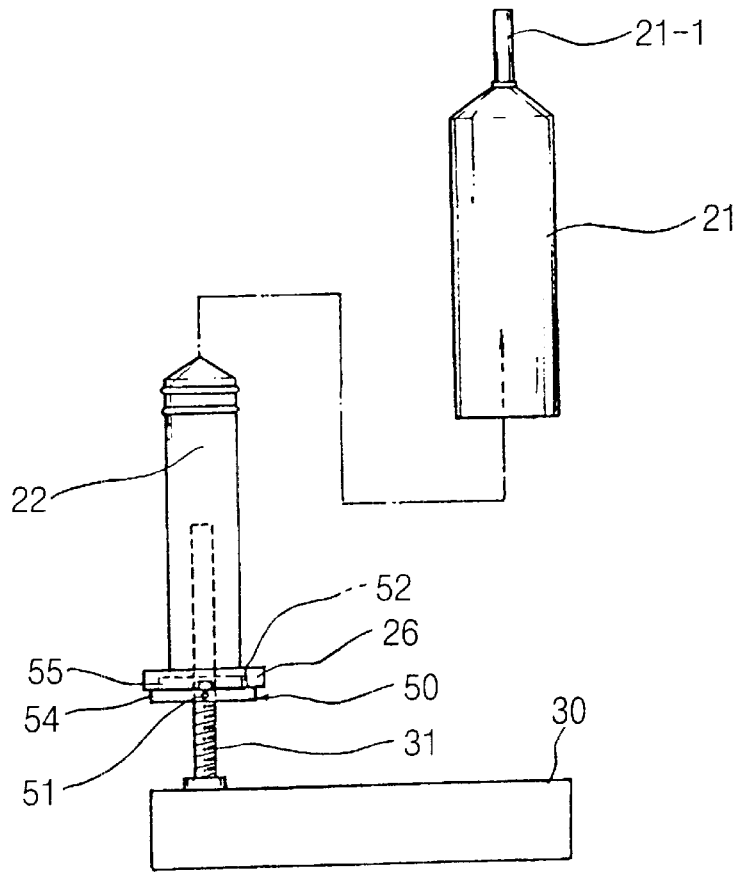
FIG. 8 is an exploded view illustrating a conventional push means.
Figure 9:
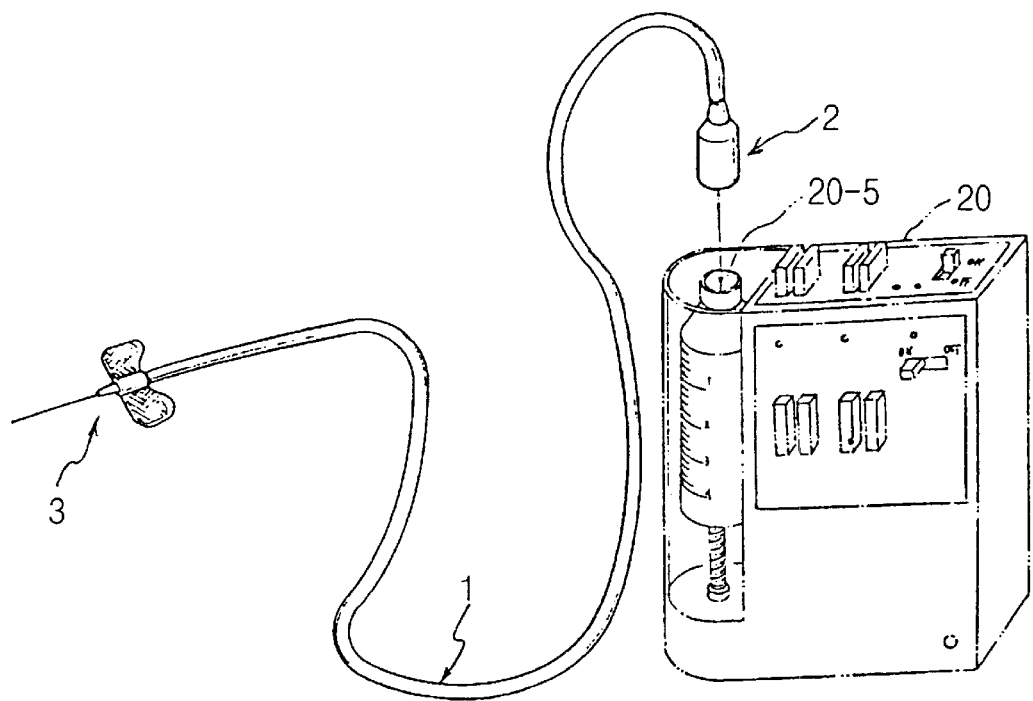
FIG. 9 is a perspective view illustrating an example of a conventional injection needle unit used for portable automatic syringe devices.
Figure 10:
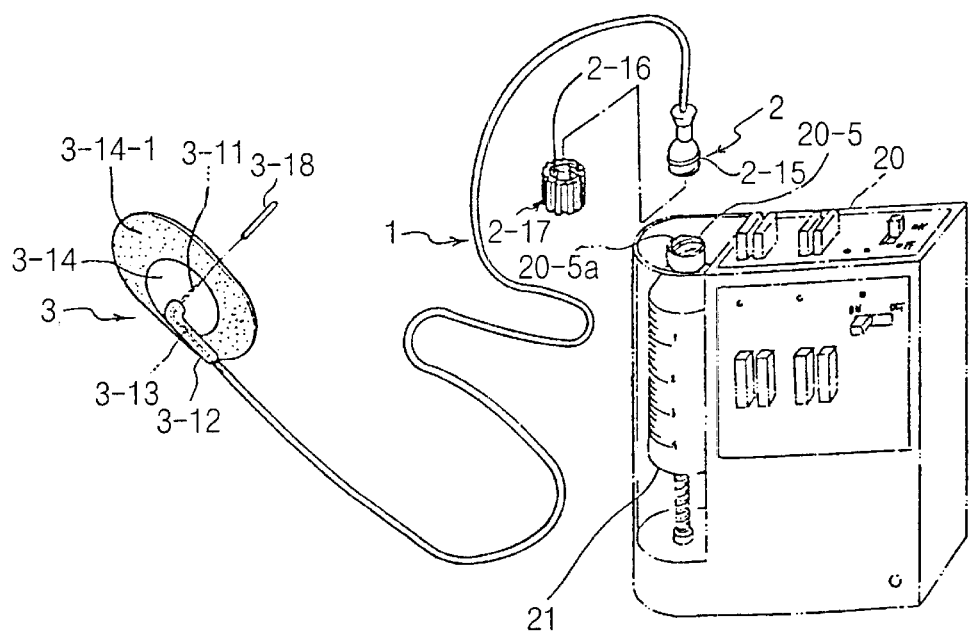
FIG. 10 is a perspective view illustrating another conventional injection needle unit.
Figure 11:
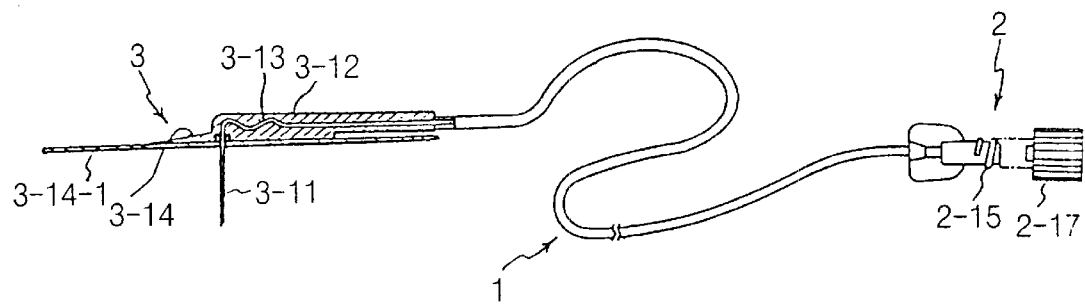
FIG. 11 is a partially-broken plan view illustrating the injection needle unit of FIG. 10.
Figure 12:
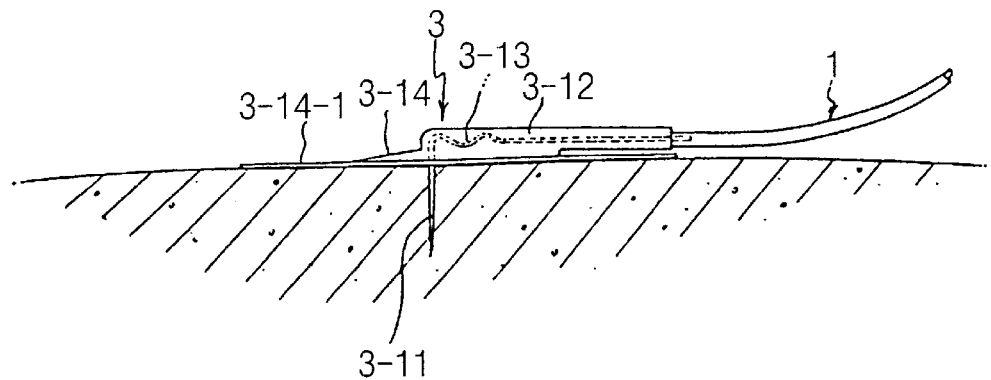
FIG. 12 is an enlarged view illustrating a using condition of the injection needle unit of FIG. 10.
Figure 13:
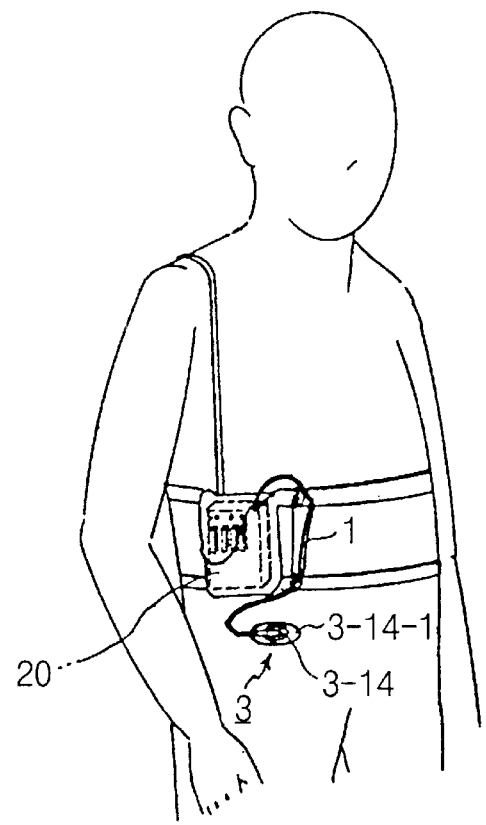
FIG. 13 is a perspective view illustrating a using condition of the injection needle unit of FIG. 10.
Figure 24:
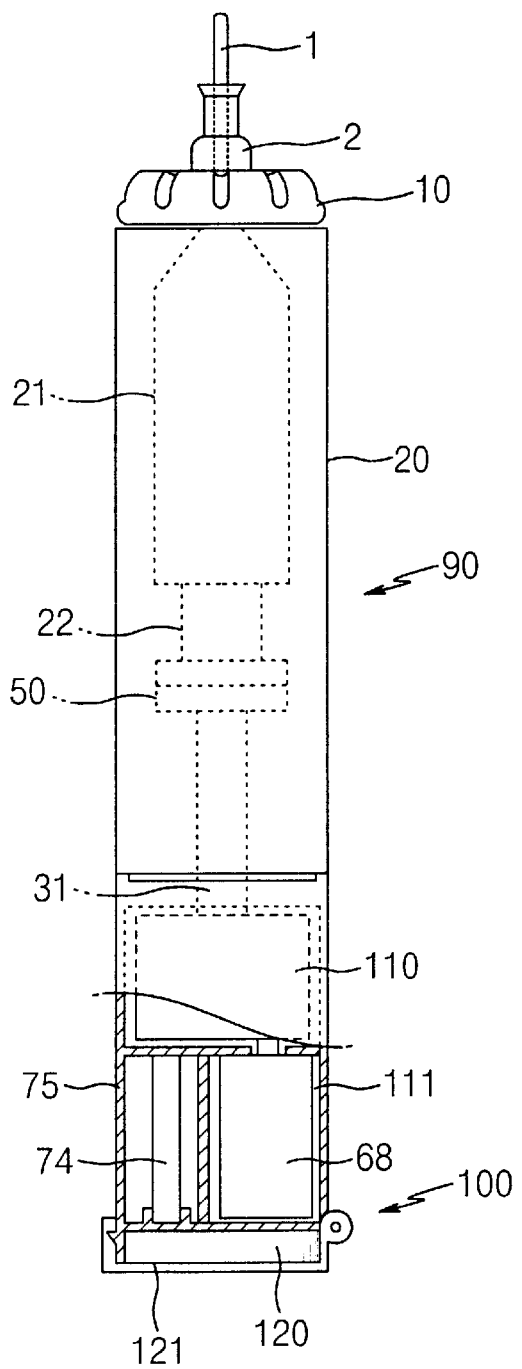
FIG. 24 is a cross-sectional view corresponding to that taken along the line B—B of FIG. 22 and illustrating another embodiment of the present invention.

As shown in FIGS. 22 to 24, the automatic syringe device of the present invention includes a syringe pump 90 having a housing 20 defined therein with a syringe receiving chamber 23 for receiving a syringe 21. The automatic syringe device also includes a reduction mechanism coupled to a rotating shaft 31 adapted to drive the syringe 21, a motor 68 for providing drive power to the reduction mechanism, and a control unit 74 mounted in the housing 20 and adapted to control the operation of the motor 68. Since the mechanical configuration of the syringe pump 90 for driving the syringe 21 by use of the drive power from the motor 68 to achieve an automatic injection of insulin is similar to the conventional configuration shown in FIG. 4, no further description thereof will be given.

In order to control the automatic injection of insulin in a remote controlled fashion, the automatic syringe device further includes a remote controller 80 in accordance with the present invention. As shown in FIG. 20, the remote controller 80 includes a control unit 81, a transmitter/receiver unit 84 controlled by the control unit 81, and a display 83 for displaying the ON or OFF state and the operation mode of the syringe pump 90. In FIG. 20, the reference numerals 82, 85, and 86 denote a key input unit, an input/output interface, and a connecting jack which are included in the remote controller 80. As shown in FIG. 21, the key input unit 82 of the remote controller 80 includes a "NEXT" key 82-1, a "SELECT" key 82-2, an "UP" key 82-3, and a "DOWN" key 82-4, and a key input confirm key 82-5. The key input confirm key 82-5 is used to check whether or not a desired key input is generated, in order to prevent an erroneous operation of the syringe pump 90.

Position recognizing protrusions 82-6 are provided at opposite sides of the key input confirm key 82-5, respectively. In FIG. 21, the reference numeral 82-7 denotes a connecting jack cover for protecting the connecting jack 86 adapted to connect the remote controller 80 with a computer for data exchange. Upon using the connecting jack 86, the connecting jack cover 86 is opened to expose the connecting jack 86. As shown in FIGS. 22 and 23, the syringe pump 90 preferably dispenses with any display means because the remote controller 80 equipped with the display 83 is used. Since the syringe pump 90 is not equipped with any display means having a substantial width, its housing 20 can have a rod shape.

The syringe pump 90 also includes a power supply unit 100 directly connected to the rotating shaft 31 in order to supply drive power to the syringe 21. The power supply unit 100 includes the motor 68, the reduction mechanism adapted to supply drive power from the motor 68 to the rotating shaft 31 in a speed-reduced state, and the control unit 74 adapted to control the operation of the motor 68. The reduction mechanism comprises a reduction gear unit 110 coupled between the motor 68 and the rotating shaft 31 to supply drive power from the motor 68 to the rotating shaft 31 in a speed-reduced state. The control unit 74 includes a transmitter/receiver unit 73 having a bidirectional signal transmission and reception function with respect to the remote controller 80. The reduction gear unit 110 is arranged at a lower portion of the housing 20. The rotating shaft 31 extends downwardly from the syringe 21 to the lower portion of the housing 20 so that it is coupled to the reduction gear unit 110. The motor 68 is received in a motor housing 111. As shown in FIG. 22, the motor housing 111 is formed at one side of the housing 20 such that it extends vertically in parallel to the rotating shaft 31. The control unit 74 is arranged at one side of the motor housing 111 such that it extends vertically in parallel to the motor housing 111.

FIG. 24 illustrates another embodiment of the present invention. This figure corresponds to a cross-sectional view taken along the line B—B of FIG. 22. In accordance with this embodiment, the motor housing 111, which receives the motor 68, extends downwardly from the lower end of the housing 20. In accordance with this embodiment, the control unit 74 is also received in a hollow extension 75 extending downwardly from the lower end of the housing 20 in parallel to the motor housing 111. By such an arrangement, the syringe pump 90 has a rod-shaped structure.

Since the basic operation of the syringe pump 90, conducted under the condition in which the syringe 21 is received in the syringe pump 90 and connected with the feeding tube 1, is the same as that of the above described conventional case, no description thereof will be given. In accordance with the present invention, however, the operation of the syringe pump 90 is conducted in a remote-controlled fashion by the remote controller 80. In particular, the remote controller 80 is equipped with the display 83. Accordingly, it is possible to check the operation of the syringe pump 90 using the remote controller 80 without directly viewing the syringe pump 90. The remote controller 80 of the present invention not only has a general remote control function, which may be provided by general remote controllers, but also has a monitoring function provided by the display 83. By virtue of such a monitoring function of the remote controller 80, it is unnecessary for the syringe pump 90 to be exposed when its operation is monitored or controlled. Accordingly, there is an advantage in that the manipulation of the remote controller 80 by the user does not cause others to recognize the fact that the user is a patient requiring use of an insulin pump.

Figure 15:
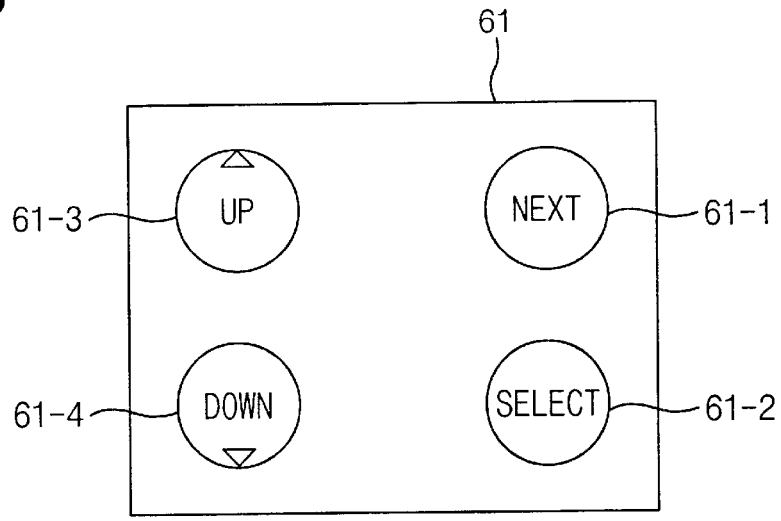
FIG. 15 is a schematic view illustrating a key input unit included in the control circuit of FIG. 14.
Figure 16A:
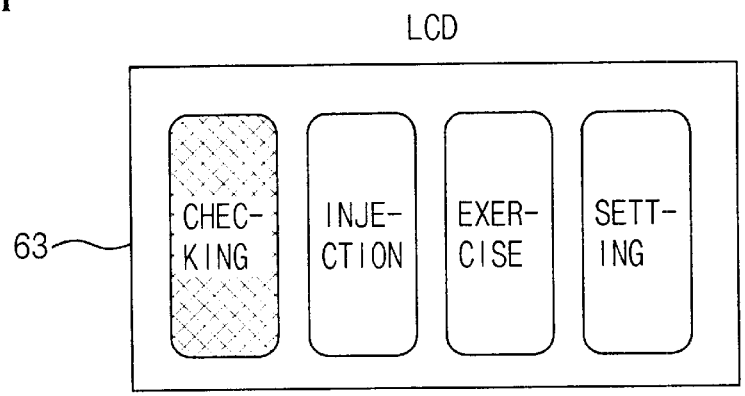
FIG. 16a is a schematic view illustrating a mode window displayed on the screen of a display included in the control circuit of FIG. 14.
Figure 16B:
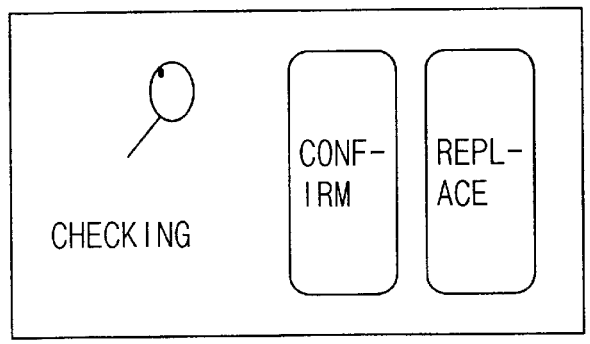
Figure 17:
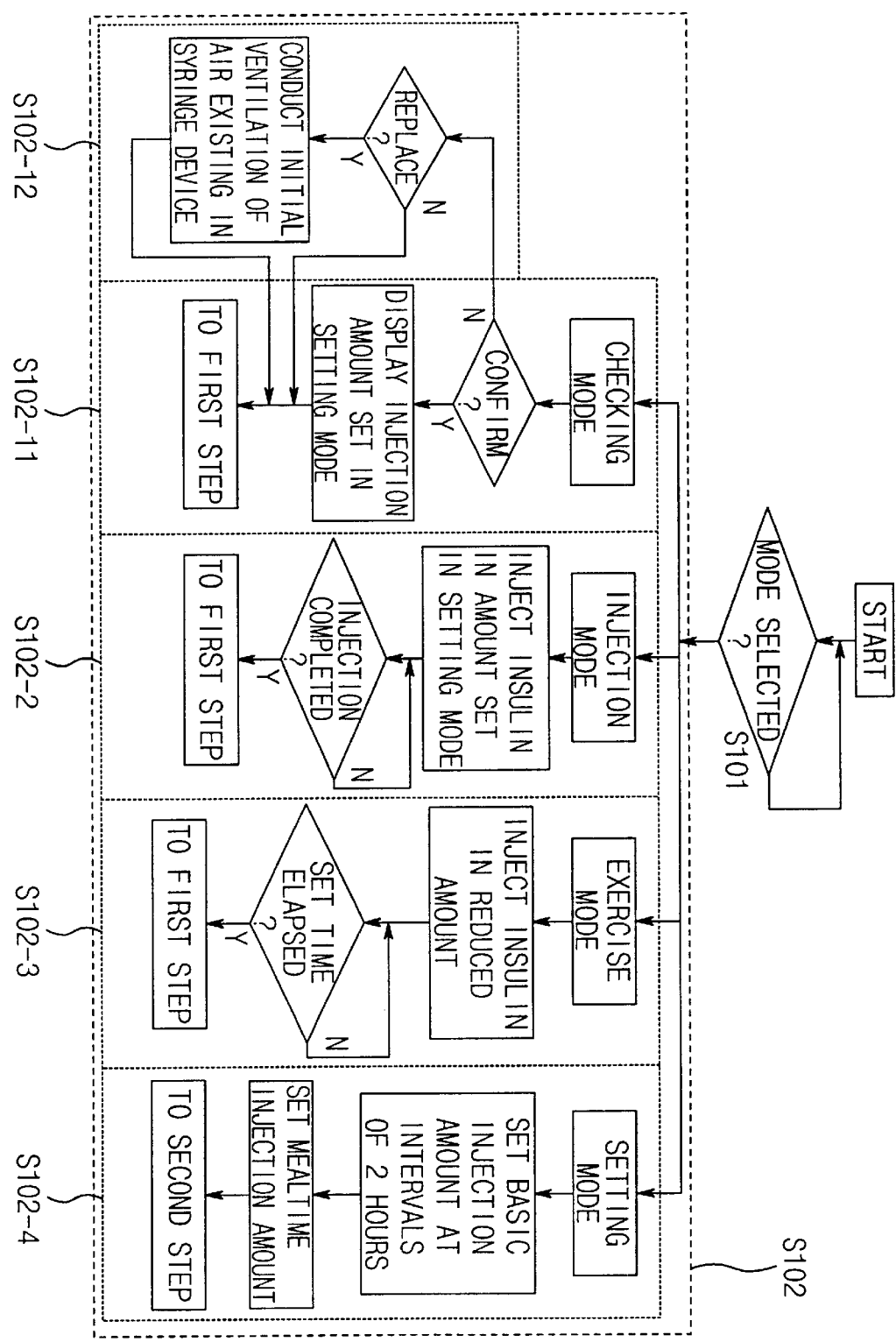
FIG. 17 is a flow chart illustrating a control procedure conducted by the control circuit of FIG. 14.
Figure 18A:
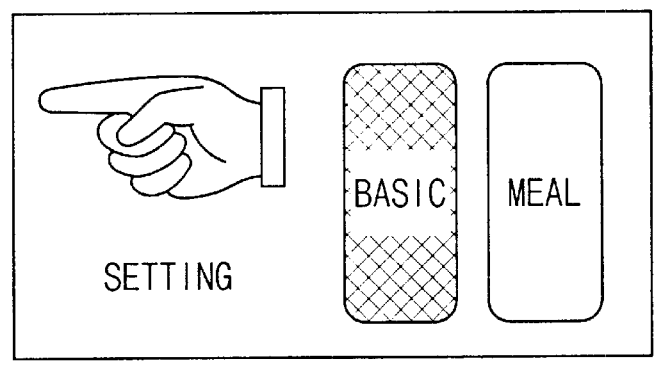
FIG. 18a is a schematic view illustrating a basic injection amount setting window displayed on the display screen of FIG. 14.
Figure 18B:
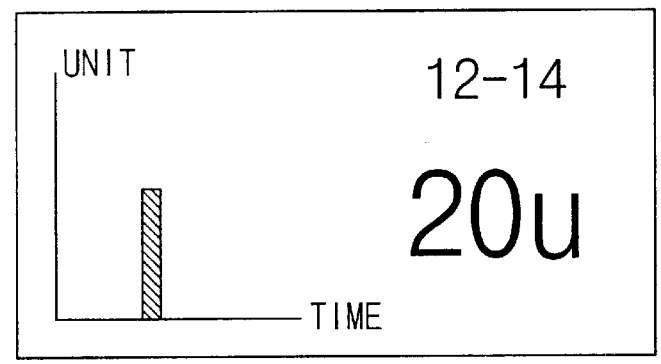
Figure 19A:
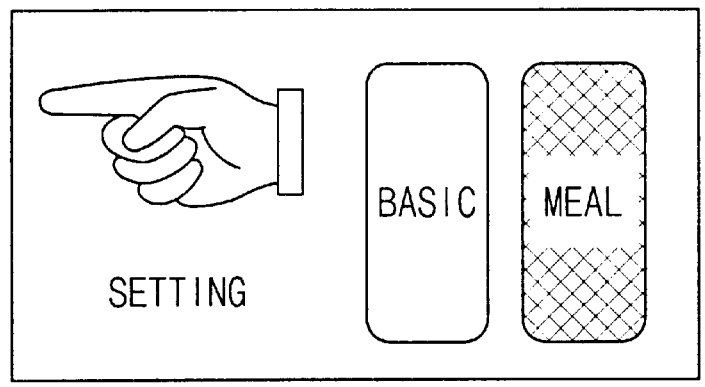
FIG. 19a is a schematic view illustrating a mealtime injection amount setting window displayed on the display screen of FIG. 14.
Figure 19B:
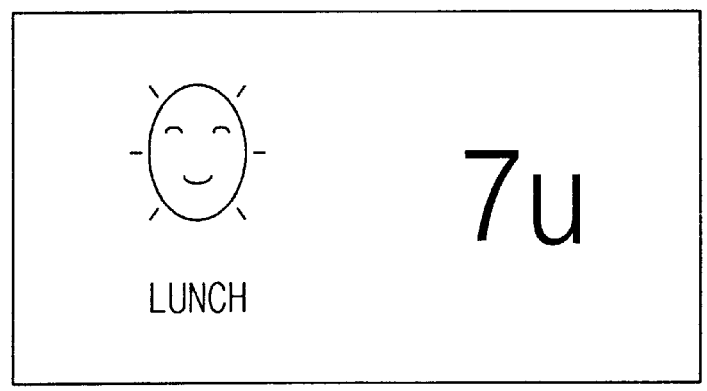

In accordance with the present invention, the remote controller 80 is provided with the key input unit 82 corresponding to the key input unit of FIG. 15 provided at the housing 20 of the conventional automatic syringe device. Accordingly, all operations and settings associated with the syringe pump 90 can be controlled or conducted by the remote controller 80. In order to prevent an erroneous operation of the syringe pump 90 due to an erroneous manipulation of the key input unit 82 by the user, the key input unit 82 also includes the key input confirm key 82-5 adapted to generate a confirm signal for allowing the control unit 81 to receive a key input generated from the key input unit 82 when the user confirms the key input as a desired one. In order to provide an enhanced security, the key input confirm key 82-5 is preferably configured to generate its confirm signal when being repeatedly depressed several times. As described above, the position recognizing protrusions 82-6 are provided at opposite sides of the key input confirm key 82-5, respectively. These position recognizing protrusions 82-6 serve to allow the user to sense the position of the key input confirm key 82-5 so that the user can manipulate the key input confirm key 82-5 only with the sense of touch even if he is a blind. By virtue of the position recognizing protrusions 82-6, the remote controller 80 can have an improved functionality.

Figure 14:
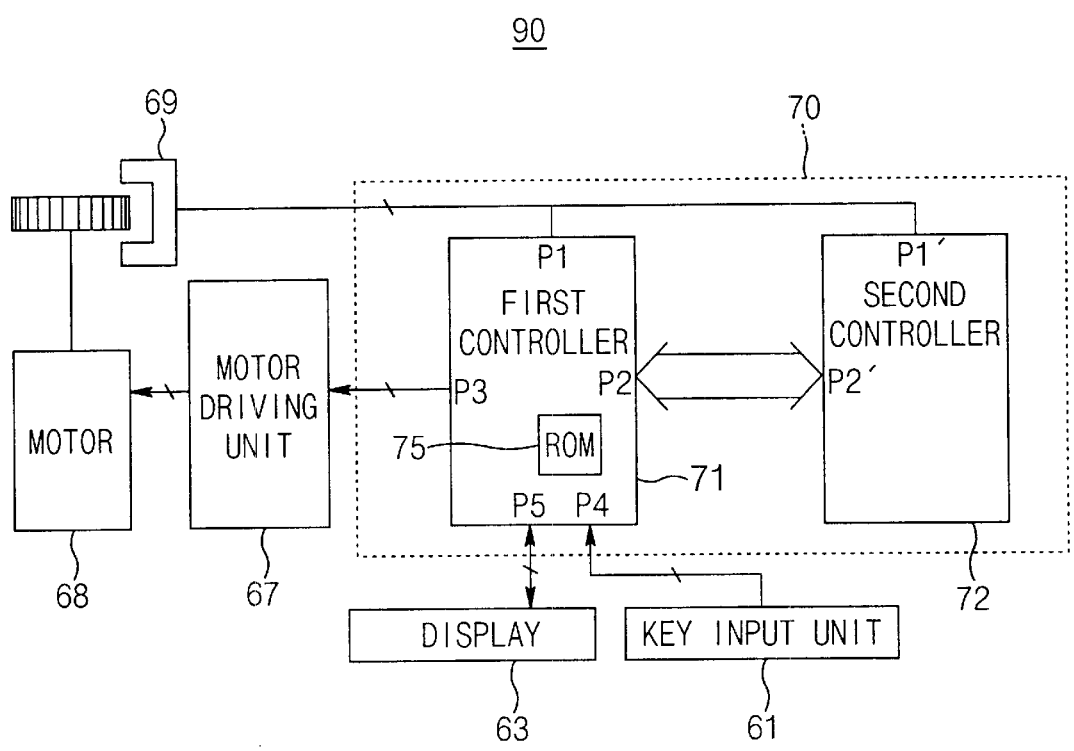
FIG. 14 is a block diagram illustrating a control circuit included in a conventional automatic syringe device.

Since no display is installed on the syringe pump 90 in accordance with the present invention, the housing 20 of the syringe pump 90 can have a reduced size. By virtue of such a reduced size, the range of positions where the syringe pump 90 is worn by the user can be extended. In conventional cases, the user has to wear a syringe device at his abdomen or to belt the syringe device on his abdomen in a state in which an injection needle connected to the syringe device via a feeding tube is penetrated into the abdomen so that he can manipulate the syringe device while viewing the operation state of the syringe device displayed on its display, for example, the display 63 shown in FIG. 14. Furthermore, the syringe device must be exposed every time it is manipulated. In accordance with the present invention, however, the syringe pump 90 has a structure in which only the power supply unit 100 extends vertically from the lower end of the housing 20 because it is unnecessary to install any display means on the syringe pump 90. That is, the syringe pump 90 has a considerably reduced width, as compared to those of the conventional cases, so that it can be held on a jacket worn by the user, like as a fountain pen. Accordingly, it is possible to control the syringe pump 90 by manipulating the remote controller 80 without attracting any attention. The user may manipulate the remote controller 80 using the key input unit 82 while viewing the display 83 provided at the remote controller 80. Although means for allowing the syringe pump 90 to be held on a jacket worn by the user, it may be implemented using appropriate means such as a strap employing hook and loop fasteners or a separate attachment case. Alternatively, such means may be provided at the outside of the housing 20. A battery 120 may be used as a power supply source for the motor 68. In order to allow the battery 120 to be replaced with a new one, a battery cover 121 may be provided at the housing 20. The transmitter/receiver unit 73 provided at the syringe pump 90 and the transmitter/receiver unit 84 provided at the remote controller 80 may be designed using diverse transmission and reception techniques. For example, they may comprise an infrared transmitter/receiver or a radio frequency transmitter/receiver.

Although the preferred embodiments of the invention have been disclosed for illustrative purposes, those skilled in the art will appreciate that various modifications, additions and substitutions are possible, without departing from the scope and spirit of the invention as disclosed in the accompanying claims.

As apparent from the above description, the present invention provides a remote-controlled portable automatic syringe device including a syringe pump configured to operate in a remote controlled fashion and a remote controller adapted to control the syringe pump and provided with a display, thereby being capable of allowing the user to conveniently control the syringe pump by use of the remote controller while viewing the display without a requirement to expose the syringe pump for a manipulation thereof. Accordingly, the automatic syringe device of the present invention has an advantage in that the privacy of the user can be secured.

Since the syringe pump dispenses with any display means, it can have a correspondingly reduced size. Accordingly, the syringe pump can be more conveniently worn by the user. In particular, the syringe pump can have a rod-shaped structure, like as a fountain pen, where its power supply unit is arranged such that it extends vertically from the lower end of a housing for the syringe pump, that is, longitudinally of the housing. In this case, the range of positions where the syringe pump is worn by the user can be extended. Accordingly, an enhanced convenience in using the automatic syringe device according to the present invention is achieved.

What is claimed is:

1. An automatic syringe device comprising a syringe containing a liquid medicine, a syringe pump having a housing defined therein with a syringe receiving chamber for receiving the syringe, a rotating shaft received in the housing and adapted to apply, to the syringe, a drive force for injecting the liquid medicine out of the syringe in accordance with a rotation thereof, a reduction mechanism received in the housing and coupled to the rotating shaft, a motor received in the housing and adapted to supply drive power to the reduction mechanism, and a first control unit received in the housing and adapted to control an operation of the motor, further comprising:

a first transmitter/receiver unit received in the housing and electrically connected to the first control unit; and a remote controller adapted to control the first control unit via the first transmitter/receiver unit, the remote controller comprising a key input unit adapted to generate a key signal in response to a manipulation thereof conducted by a user, a second control unit adapted to receive the key signal from the key input unit and to conduct a control operation in response to the received key signal, a second transmitter/receiver unit electrically connected to the second control unit and adapted to conduct transmission and reception of signals to and from the first transmitter/receiver unit under a control of the second control unit, and a display electrically connected to the second control unit and adapted to display an ON or OFF state and an operation mode of the syringe pump under a control of the second control unit, whereby the user is allowed to control the syringe pump by use of the remote controller while viewing the display of the remote controller without a requirement to expose the syringe pump for a manipulation thereof.

2. The automatic syringe device according to claim 1, wherein the key input unit of the remote controller comprises a "NEXT" key, a "SELECT" key, an "UP" key, a "DOWN" key, and a key input confirm key adapted to prevent an erroneous operation of the syringe pump due to an erroneous manipulation of the key input unit by the user.

3. The automatic syringe device according to claim 2, wherein the key input unit of the remote controller further comprises position recognizing protrusions provided at opposite sides of the key input confirm key, respectively.

4. The automatic syringe device according to claim 2, wherein the key input confirm key generates a confirm signal for allowing the control unit of the remote controller to receive a key input generated from the key input unit, when it is repeatedly depressed a predetermined number of times.

5. The automatic syringe device according to claim 1, further comprising:

a motor housing formed at one side of the housing while extending vertically in parallel to the rotating shaft, the motor housing serving to receive the motor therein.

6. The automatic syringe device according to claim 1, further comprising:

a motor housing extending downwardly from a lower end of the housing and receiving the motor therein; and a hollow extension extending downwardly from the lower end of the housing in parallel to the motor housing and receiving the first control unit therein, whereby the syringe pump has a rod-shaped structure.

* * * * *